(12) United States Patent
Dubois

(10) Patent No.: US 8,450,509 B2
(45) Date of Patent: May 28, 2013

(54) METHOD FOR SYNTHESISING 9-AMINONONANOIC ACID OR THE ESTERS THEREOF FROM NATURAL UNSATURATED FATTY ACIDS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 248 days.

(21) Appl. No.: 13/001,659

(22) PCT Filed: Jul. 9, 2009

(86) PCT No.: PCT/FR2009/051370
§ 371 (c)(1),
(2), (4) Date: Dec. 28, 2010

(87) PCT Pub. No.: WO2010/004220
PCT Pub. Date: Jan. 14, 2010

(65) Prior Publication Data
US 2011/0105774 A1 May 5, 2011

(30) Foreign Application Priority Data
Jul. 10, 2008 (FR) .................................. 08 54708

(51) Int. Cl.
*C07C 227/00* (2006.01)
*C07C 229/00* (2006.01)

(52) U.S. Cl.
USPC ........... 554/114; 560/155; 562/553; 554/111; 554/132; 554/161

(58) Field of Classification Search
None
See application file for complete search history.

(56) References Cited

U.S. PATENT DOCUMENTS 5,973,208 A 10/1999 Nagareda et al.

FOREIGN PATENT DOCUMENTS

GB 743491 1/1956
WO WO2008/046106 4/2008

OTHER PUBLICATIONS

Aharoni, S., "n-Nylons: Their Synthesis, Structure, and Properties" John Wiley & Sons, (1997), pp. 381-389.
Pryde, E., et al., "Aldehydic Materials by the Ozonization of Vegetable Oils", The Journal of the American Oil Chemists Society, (1962), pp. 496-500.
Throckmorton, P., "Pilot Run, Plant Design and Cost Analysis for Reductive Ozonolysis of Methyl Soyate", The Journal of the American Oil Chemists Society, (1972), pp. 643-648.
Perkins, R., et al., "Nylon-9 from Unsaturated Fatty Derivatives: Preparation and Characterization", The Journal of the American Oil Chemists Society, (1975), pp. 473-477.
Drawert, F., et al., "Bildung von 9-Oxo-nonansauremethylester und 12-Oxo-dodecensauremethylester aus Linol-und Linolsauremethylester und von 9-Oxo-nonansaure aus Sonnenblumenol durch Bestrahlung mit 6 Mrad*", Chem. Mikrobol. Technol. Lebensm, (1972), pp. 158-159.
Zhang, G., et al., "Study on Oxidations of Benzilic Ethers, Oximes and 1,2-Diols by Ammonium Chlorochromate", Chinese Chemical Letters, (1994), pp. 105-108.
Schwartz, C., et al., "Reductive ozonolysis' via a new fragmentation of carbonyl oxides", Tetrahedron, (2006), pp. 10747-10752.
Mol, J., "Catalytic metathesis of unsaturated fatty acid esters and oils*", Topics in Catalysis, (2004), pp. 97-104.
Schaverien, C., et al., "A Well-Characterized, Highly Active, Lewis Acid Free Olefin Metathesis Catalyst", J. Am. Chem. Soc., (1986), pp. 2771-2773.
Couturier, J.-L., et al., "A Cyclometalated Aryloxy(chloro)neopentylidenetungsten Complex: A Highly Active and Stereoselective Catalyst for the Metathesis of cis- and trans-2-Pentene, Norbornene, 1-Methylnorbornene, and Ethyl Oleate**", Angew. Chem. Int. Ed. Engl., (1992), pp. 628-631.
Schwab, P., et al., "A Series of Well-Defined Metathesis Catalysts Synthesis of [RuCl2 (=CHR)(PR3)2]and Its Reactions**", Angew. Chem. Int. Ed. Engl., (1995) pp. 2039-2041.
Scholl, M., et al., "Synthesis and Activity of a New Generation of Ruthenium-Based Olefin Metathesis Catalysts Coordinated with 1,3-Dimesityl-4, 5-dihydroimidazol-2-ylidene Ligands", Organic Letters, (1999), pp. 953-956.
Miller, W., et al., "Nylon-9 Via 9-Aminononanoic Acid from Soybean Oil", Ind. Eng. Chem. Prod. Res. Develop., (1971), pp. 442-447.
Kohlhase, W. et al., "9-Aminononanamide and Nylon-9 From Azelaaldehydic Derivatives of Soybean Oil", Journal of the American Oil Chemists Society, (1970), pp. 183-188.
Mol, J., "Application of olefin metathesis in oleochemistry: an example of green chemistry", The Royal Society of Chemistry, (2002), pp. 5-13.

*Primary Examiner* — Yate K Cutliff
(74) *Attorney, Agent, or Firm* — Smith, Gambrell & Russell, LLP

(57) ABSTRACT

The invention relates to a method for synthesizing 9-aminononanoic acid or the esters thereof from natural unsaturated fatty acids, comprising at least one step of metathesis of the natural fatty acid and an oxidation step by oxidative cleaving. Said synthetic method uses widely available renewable starting materials and hence economical.

5 Claims, No Drawings

METHOD FOR SYNTHESISING 9-AMINONONANOIC ACID OR THE ESTERS THEREOF FROM NATURAL UNSATURATED FATTY ACIDS

FIELD OF THE INVENTION

The invention is targeted at a process for the synthesis of 9-aminononanoic acid or its esters from natural unsaturated fatty acids comprising at least one stage of metathesis of the natural fatty acid and a stage of oxidation by oxidative cleavage.

BACKGROUND OF THE INVENTION

The polyamides industry uses a whole range of monomers consisting of long-chain ω-amino acids, normally known as Nylon, characterized by the length of methylene chain $(-CH_2-)_n$ separating two amide functional groups $-CO-NH-$. Thus it is that Nylon 6, Nylon 6,6, Nylon 6,10, Nylon 7, Nylon 8, Nylon 9, Nylon 11, Nylon 13, and the like, are known.

These monomers are, for example, manufactured by a chemical synthesis route using in particular, as starting material, $C_2$ to $C_4$ olefins, cycloalkanes or benzene but also castor oil (Nylon 11), erucic or lesquerolic oil (Nylon 13), and the like.

Current developments with regard to the environment are resulting in the use of natural starting materials originating from a renewal source being favored in the fields of energy and chemistry. This is the reason why some studies have been taken up to develop, industrially, processes using fatty acids/esters as starting material in the manufacture of these monomers.

This type of approach has only a few industrial examples. One of the rare examples of an industrial process using a fatty acid as starting material is that of the manufacture, from the ricinoleic acid extracted from castor oil, of 11-aminoundecanoic acid, which forms the basis of the synthesis of Rilsan 11®. This process is described in the work "Les Arocédés de Pétrochimie" [Petrochemical Processes] by A. Chauvel et al., which appeared in Editions Technip (1986). 11-Aminoundecanoic acid is obtained in several stages. The first consists of a methanolysis of castor oil in a basic medium, producing methyl ricinoleate, which is subsequently subjected to a pyrolysis in order to obtain, on the one hand, heptanaldehyde and, on the other hand, methyl undecylenate. The latter is converted to the acid form by hydrolysis. Subsequently, the acid formed is subjected to a hydrobromination to give the ω-brominated acid, which is converted by amination to 11-aminoundecanoic acid.

The process of the invention is targeted at the synthesis of 9-aminononanoic acid or 9-aminoazelaic acid corresponding to Nylon 9. As regards this specific monomer, mention may be made of the work "n-Nylons, Their Synthesis, Structure and Properties", 1997, published by J. Wiley and Sons, chapter 2.9 (pages 381 to 389) of which is devoted to Nylon 9. This article summarizes the preparations and studies carried out with regard to the subject. Mention is made therein, on page 381, of the process developed by the former Soviet Union which has resulted in the commercialization of Pelargon®. Mention is also made therein, on page 384, of a process developed in Japan which uses oleic acid originating from soybean oil as starting material. The corresponding description makes reference to the work by A. Ravve "Organic Chemistry of Macromolecules" (1967) Marcel Dekker, Inc., part 15 of which is devoted to polyamides and which mentions, on page 279, the existence of such a process.

In order to be fully informed with regard to the state of the art on this subject, mention should be made of the numerous papers published by E. H. Pryde et al. between 1962 and 1975 in the Journal of the American Oil Chemists' Society—"Aldehydic Materials by the Ozonization of Vegetable Oils" Vol. 39, pages 496-500; "Pilot Run, Plant Design and Cost Analysis for Reductive Ozonolysis of Methyl Soyate" Vol. 49, pages 643-648 and R. B. Perkins et al. "Nylon-9 from Unsaturated Fatty Derivatives: Preparation and Characterization" JAOCS, Vol. 52, pages 473-477. It should be noted that the first of these papers also make reference, on page 498, to previous studies carried out by the Japanese authors H. Otsuki and H. Funahashi.

To summarize this state of the art targeted at the synthesis of "Nylon 9" from vegetable oils, a description may be given of the following simplified reaction mechanism applied to the oleic ester extracted from the oils by methanolysis:

Reductive Ozonolysis

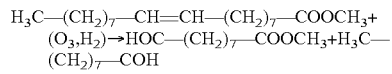

Reductive Amination

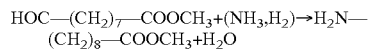

Hydrolysis

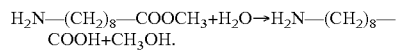

However, this route, which is very attractive from the reaction viewpoint, exhibits a significant economic drawback consisting of the production, during the first stage, of a long-chain aldehyde (9 carbon atoms in total) which in practice cannot be recovered in value, in particular in the polymer industry relating to polyamides.

DETAILED DESCRIPTION OF THE INVENTION

The present invention is targeted at overcoming this major drawback by providing a process based on a similar reaction process but which makes possible the synthesis of a range of compounds which can be easily recovered in value.

The problem is thus that of finding a process for the synthesis of an ω-amino acid of formula $H_2N-(CH_2)_8-COOH$ (and of its polymer), starting from very widely accessible and therefore inexpensive renewable starting materials, which is simple to carry out while avoiding, on the one hand, the environmental constraints mentioned above and, on the other hand, the economic handicaps due to the by-products from the reactions.

The solution provided consists in working from starting materials consisting of natural long-chain unsaturated fatty acids. The term "natural fatty acids" is understood to mean an acid resulting from the plant or animal milieu, including algae, more generally from the plant kingdom, and thus renewable. This acid will comprise at least one olefinic unsaturation located in the 9 position with respect to the acid group (δ9) and will comprise at least 10 and preferably at least 14 carbon atoms per molecule.

Mention may be made, as examples of such acids, of caproleic acid (9-decenoic acid), myristoleic acid (cis-9-tetradecanoic acid), palmitoleic acid (cis-9-hexadecanoic acid), the $C_{18}$ acids, oleic acid (cis-9-octadecanoic acid), elaidic acid (trans-9-octadecanoic acid), linoleic acids (cis,cis-9,12-octadecadienoic acid and cis,trans-9,11-octadecadienoic acid), α-linolenic acid (cis,cis,cis-9,12,15-octadecatrienoic acid), α-eleostearic acid (cis,trans,trans-9,11,13-octadeca-trienoic acid) or the hydroxylated fatty acid ricinoleic acid (12-hydroxy-cis-9-octadecenoic acid), and gadoleic acid (cis-9-eicosenoic acid).

These various acids result from the vegetable oils extracted from various plants, such as the sunflower, rape, the castor oil plant, the olive, soya, the palm tree, the avocado or the common sea buckthorn.

They also result from the terrestrial or marine animal world and, in the latter case, both in the fish or mammal form and in the algal form. They are then generally fats originating from ruminants, fish, such as the cod, or marine mammals, such as whales or dolphins.

A subject matter of the invention is a process for the synthesis of amino acids or amino esters of general formula $NH_2—(CH_2)_8—COOR$, R being either H or an alkyl radical comprising from 1 to 4 carbon atoms, from long-chain natural unsaturated fatty acids or esters corresponding to the formula $R_1CH=CH—(CH_2)_7—COOR$ in which $R_1$ represents either H or a hydrocarbon radical comprising from 1 to 11 carbon atoms, comprising from 0 to 2 olefinic unsaturations and, if appropriate, comprising one hydroxyl functional group, which consists, in a first stage, in subjecting said unsaturated fatty acid or ester to a catalytic cross metathesis reaction with ethylene to form ω-unsaturated acids or esters, at least 50 mol % of which correspond to the formula $CH_2=CH—(CH_2)_7—COOR$, then, in a second stage, in subjecting the acid or ester of formula $CH_2=CH—(CH_2)_7—COOR$ to an oxidative cleavage reaction to form an aldehyde acid/ester of formula $CHO—(CH_2)_7—COOR$ and then, finally, in converting the resulting product by reductive amination to give an ω-amino acid/ester (unless it has been said in the text that acid should be understood as acid or ester) of formula $NH_2—(CH_2)_8—COOR$.

The reaction process can be summarized as follows, applied to oleic acid:

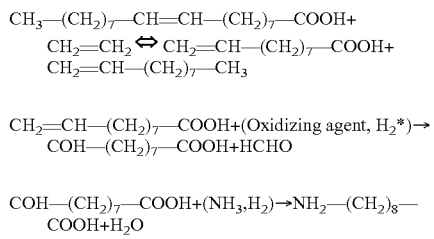

H2* symbolizes, in reaction 2, the coupling of an oxidation followed by a reduction.

The only "by-products" formed are a long-chain α-olefin and formaldehyde.

The cross metathesis reaction with ethylene (ethenolysis) is carried out under conditions which are fully known. The reaction temperature is between 20 and 100° C. at atmospheric pressure in the presence of a ruthenium-based catalyst.

The ruthenium catalysts are preferably chosen from the charged or uncharged catalysts of general formula:

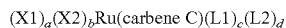

in which:
a, b, c and d are integers with a and b equal to 0, 1 or 2 and c and d equal to 0, 1, 2, 3 or 4;
X1 and X2, which are identical or different, each represent a charged or uncharged and mono- or multichelating ligand; mention may be made, by way of examples, of halides, sulfate, carbonate, carboxylates, alkoxides, phenates, amides, tosylate, hexafluoro-phosphate, tetrafluoroborate, bistriflylamide, tetra-phenylborate and derivatives. X1 or X2 can be bonded to Y1 or Y2 or to the (carbene C) so as to form a bidentate ligand (or chelate) on the ruthenium; and
L1 and L2, which are identical or different, are electron-donating ligands, such as phosphine, phosphite, phosphonite, phosphinite, arsine, stilbene, an olefin or an aromatic, a carbonyl compound, an ether, an alcohol, an amine, a pyridine or a derivative, an imine, a thioether or a heterocyclic carbene,
L1 or L2 can be bonded to the "carbene C" so as to form a bidentate ligand or chelate, The "carbene C" can be represented by the general formula: C_(R1)_(R2) for which R1 and R2 are identical or different, such as hydrogen or any other saturated or unsaturated, cyclic, branched or linear, or aromatic hydrocarbonyl group. Mention may be made, by way of examples, of alkylidene or cumulene complexes of ruthenium, such as vinylidenes Ru=C=CHR or allenylidenes Ru=C=C=CR1R2 or indenylidenes.

A functional group which makes it possible to improve the retention of the ruthenium complex in the ionic liquid can be grafted to at least one of the ligands X1, X2, L1 or L2 or to the carbene C. This functional group can be charged or uncharged, such as, preferably, an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The oxidative cleavage reaction on the double bond, which results in the formation of aldehyde functional groups on the two carbons of the double bond, is also known per se.

It can be carried out by means of a strong oxidizing agent, such as $KMnO_4$ in a concentrated form and with heating, as is described in "Organic Chemistry" by L. G. Wade Jr., 5th edition, Chapter 8, Reactions of Alkenes. The oxidative cleavage can be carried out with aqueous hydrogen peroxide solution, as described in the patent GB 743 491. The paper by F. Drawert et al. in Chem. Mikrobiol. Technol. Lebensm., 1, 158-159 (1972), describes an alternative route by irradiation of sunflower oil. Moreover, the paper by G. S. Mang et al. in Chinese Chemical Letters, Vol. 5, No. 2, pp 105-108, 1994, indicates that it is possible to carry out the oxidative cleavage starting from the corresponding diol of oleic acid (see Entry 29 of the table). This oxidative cleavage is carried out using ammonium chlorochromate as oxidizing agent. For its part, the diol is obtained by epoxidation of oleic acid, followed by hydrolysis of the epoxy bridge. It can be carried out with other oxidizing agents, such as aqueous hydrogen peroxide solution and more particularly ozone.

However, it is necessary to prevent the oxidation reaction from being complete. This is because the oxidation of an unsaturated acid is the well-known synthetic route for the manufacture of diacids. There is therefore good reason to provide operating conditions such that the reaction stops at the aldehyde functional group. This is the reason why, during the studies described in the prior art, attention had been paid to the hydrogenation and/or to the reduction of the products of the oxidation (ozonide), very generally by reductive ozonolysis. The oxidation conditions can thus be carried out under milder conditions and thus better control the process by operating in the presence of hydrogen and/or of a mild reducing agent. It is this reaction which is referred to as reductive ozonolysis.

The ozonolysis reaction has formed the subject of major studies which have made it possible to extricate a "Criegee" reaction mechanism (cf. paper "Aldehydic Materials by the Ozonization of Vegetable Oils" Vol. 39, pages 496-500, cited above) marked by the formation of an ozonide.

The first phase of the reductive ozonolysis can be carried out in different solvent media. If it is carried out in an aqueous phase, the unsaturated fatty acid is present in the form of a water-in-oil emulsion. It can be carried out in a solvent of alcohol type: methanol, ethanol, propanol, butanol, methoxyethanol, cyclohexanol or benzyl alcohol; in the case where the ozonolysis is carried out on the fatty ester, it will be advantageous to use the alcohol R—OH corresponding to the fatty ester. The proposal has also been made, by Chris Schwartz, Joseph Raible, Kyle Mott and Patrick. H. Dussault, *Tetrahedron*, 62 (2006), pp. 10747-10752, to use DMSO as solvent medium. It is often possible to combine an organic acid, generally acetic acid, with the alcohol solvent medium, which acid will generally be present in the form of an equimolecular mixture with the alcohol.

The second phase of the reductive ozonolysis will consist of a reduction of the ozonide, which can be carried out with zinc in acetic acid, by hydrogenation in the presence of a hydrogenation catalyst (for example Pd) or using a reducing agent, such as, for example, dimethyl sulfide (DMS).

The preferred alternative embodiment of this stage is the reductive ozonolysis, which can be carried out in the presence of zinc metal, in the powder form, or also, preferably, in the presence of dimethyl sulfide (DMS: $CH_3-S-CH_3$); this is because this DMS will be converted during the reductive ozonolysis to DMSO, a solvent widely used industrially.

Finally, the reductive amination of the aldehyde functional group to give a primary amine is well known to a person skilled in the art. The reductive amination of the 9-oxononanoic acid obtained in order to form 9-amino-nonanoic acid can be carried out according to numerous catalytic or enzymatic methods, for example according to the method described in the patent application U.S. Pat. No. 5,973,208.

In an alternative embodiment of the process of the invention, an intermediate stage can be added to the process of the invention. The process would then appear as follows (starting from the acid or from the ester):

$1^{st}$ stage: ethenolysis of the fatty acid

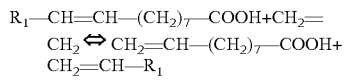

$2^{nd}$ stage: after separation of the olefin, for example by stripping, homometathesis of the 9-decenoic acid

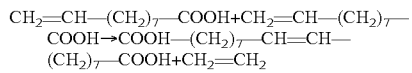

$3^{rd}$ stage: oxidative cleavage (reductive ozonolysis)

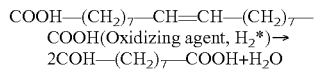

$4^{th}$ stage: reductive amination

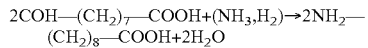

$H_2^*$ symbolizes, in reaction 3, the coupling of an oxidation followed by reduction.

In the process of the invention, the fatty acid can be treated either in its acid form or its ester form. The entirely commonplace change from one form to another, by methanolysis, esterification or hydrolysis, does not constitute a chemical conversion within the meaning of the process.

Thus, in one embodiment of the invention, on completion of the first stage, the α-olefin is separated from the medium in order to subject the unsaturated acid/ester of formula $CH_2=CH-(CH_2)_7-COOR$, during a second stage, to a homometathesis in order to form the diacid (diester) of formula $ROOC-(CH_2)_7-CH=CH-(CH_2)_7-COOR$, then, in a third stage, the diacid (diester) $COOR-(CH_2)_7-CH=CH-(CH_2)_7-COOR$ is subjected to an oxidative cleavage reaction to form an aldehyde acid of formula $CHO-(CH_2)_7-COOR$ and then, finally, in a fourth stage, the resulting product is converted by reductive amination to give an ω-amino acid/ester of formula $NH_2-(CH_2)_8-COOR$.

All the mechanisms described in detail below illustrate, in order to facilitate the account, the synthesis of the acids. However, the metathesis is as effective with an ester and even more effective, the medium generally being more anhydrous. In the same way, the schemes illustrate reactions with the cis isomer of the acids (or esters); the mechanisms are just as easily applicable to the trans isomers.

The reaction mechanism of this reaction is illustrated by scheme 1 below.

Scheme 1

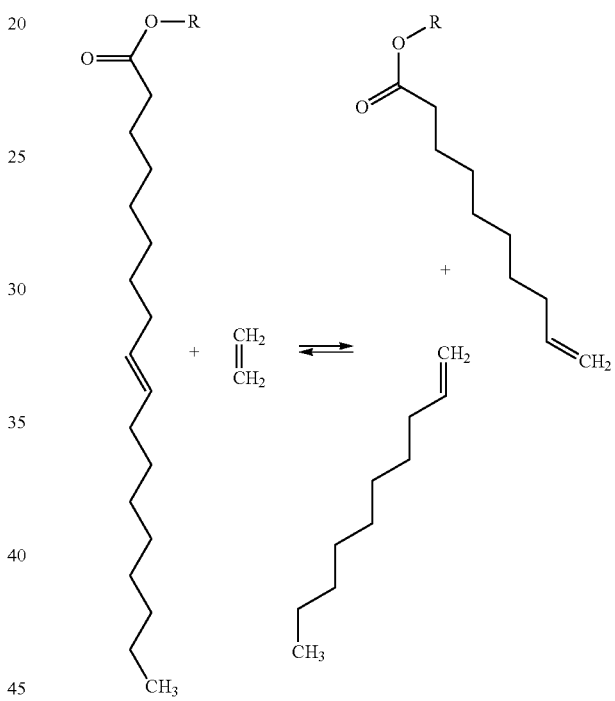

The homometathesis of the ω-olefinic acid is illustrated in scheme 2.

Scheme 2

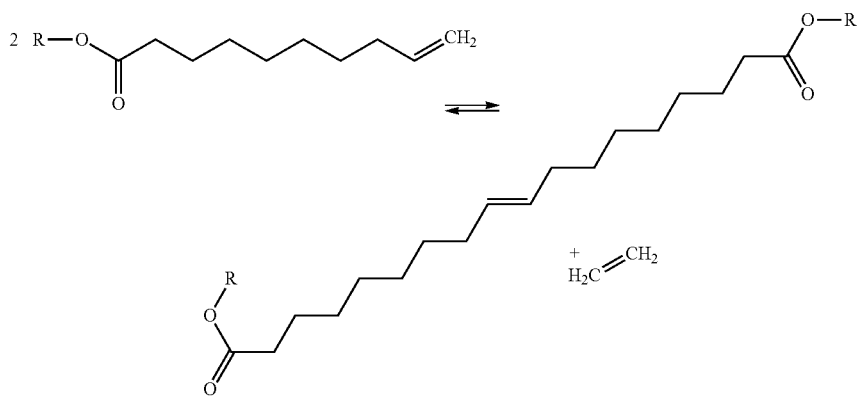

The reductive ozonolysis of the diacid or of the ω-nonenoic acid is illustrated in scheme 3.

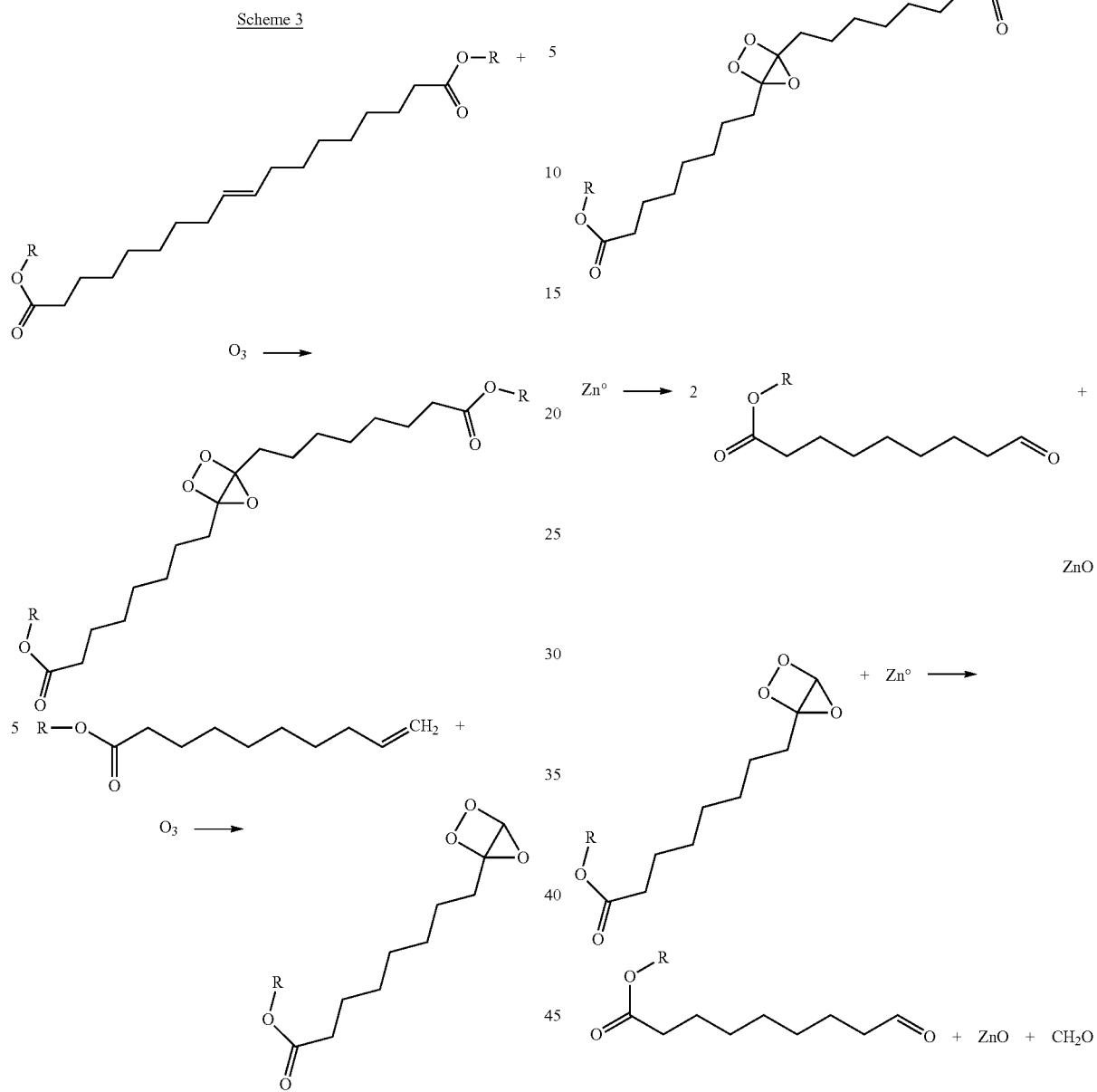

The reductive amination is illustrated in scheme 4.

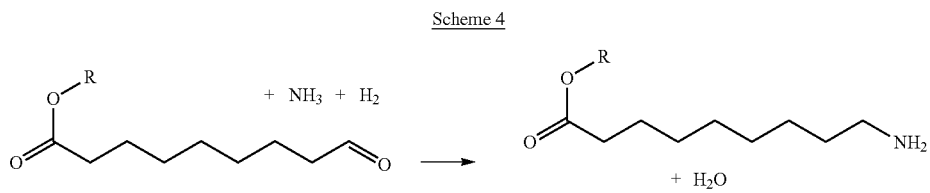

The metathesis reactions have been known for a long time, even if their industrial applications are relatively limited. Reference may be made, with regard to their use in the conversion of fatty acids (esters), to the paper by J. C. Mol "Catalytic metathesis of unsaturated fatty acid esters and oil", which appeared in Topics in Catalysis, Vol. 27, Nos. 1-4, February 2004 (Plenum Publishing Corporation).

The catalysis of the metathesis reaction has formed the subject of a great many studies and the development of sophisticated catalytic systems. Mention may be made, for example, of the tungsten complexes developed by Schrock et al. (J. Am. Chem. Soc., 108 (1986), 2771) or Basset et al. (Angew. Chem. Ed. Engl., 31 (1992), 628). The "Grubbs" catalysts (Grubbs et al., Angew. Chem. Ed. Engl., 34 (1995), 2039, and Organic Lett., 1 (1999), 953), which are ruthenium-benzylidene complexes, have appeared more recently. This concerns homogeneous catalysis. Heterogeneous catalysts based on metals, such as ruthenium, molybdenum and tungsten, deposited on alumina or silica have also been developed. Finally, studies have been carried out for the preparation of immobilized catalysts, that is to say of catalysts having an active principle which is that of the homogeneous catalyst, in particular the ruthenium-carbene complexes, but which is immobilized on an inactive support. The object of these studies is to increase the selectivity of the cross metathesis reaction with regard to the side reactions, such as the "homometatheses", between the reactants brought into contact. They relate not only to the structure of the catalysts but also to the effect of the reaction medium and the additives which may be introduced.

In the process of the invention, any active and selective metathesis catalyst can be used. However, use will preferably be made of ruthenium-based catalysts.

The cross metathesis reaction of the first stage is carried out at a temperature of between 20 and 100° C. at a pressure of 1 to 30 bar in the presence of a conventional metathesis catalyst, for example of Ruthenium type. The reaction time is chosen as a function of the reactants employed and in order to reach as close as possible to the reaction equilibrium. The reaction is carried out under an ethylene pressure.

The homometathesis reaction of the second stage is carried out at a temperature of between 20 and 100° C. at a pressure of less than 5 bar, making it possible to continuously withdraw the ethylene, this being done with a ruthenium catalyst of the type of those described above.

The invention additionally relates to the amino acid or amino ester of renewable origin of general formula $NH_2$—$(CH_2)_8$—COOK, R being either H or an alkyl radical comprising from 1 to 4 carbon atoms.

The term "amino acids or amino esters of renewable origin" is understood to mean the amino acids or amino esters which comprise carbon of renewable origin.

This is because, unlike the materials resulting from fossil materials, the materials composed in part of renewable starting materials comprise $^{14}C$. All the carbon samples drawn from living organisms (animal or plant organisms) are in fact a mixture of 3 isotopes: $^{12}C$ (representing~98.892%), $^{13}C$ (~1.108%) and $^{14}C$ (traces: $1.2\times10^{-10}$%). The $^{14}C/^{12}C$ ratio of the living tissues is identical to that of the atmosphere. In the environment, $^{14}C$ exists in two predominant forms: in the inorganic form, that is to say in the form of carbon dioxide gas ($CO_2$), and in the organic form, that is to say in the form of carbon incorporated in organic molecules.

In a living organism, the $^{14}C/^{12}C$ ratio is kept constant by the metabolism as the carbon is continually exchanged with the environment. As the proportion of $^{14}C$ is constant in the atmosphere, it is the same in the organism, as long as it is living, since it absorbs the $^{14}C$ as it absorbs the $^{12}C$. The $^{14}C/^{12}C$ mean ratio is equal to $1.2\times10^{-12}$.

$^{12}C$ is stable, that is to say that the number of $^{12}C$ atoms in a given sample is constant over time. For its part, $^{14}C$ is radioactive and each gram of carbon of a living being comprises sufficient $^{14}C$ isotope to give 13.6 disintegrations per minute.

The half-life (or T1/2 period) is the time at the end of which any number of radioactive nuclei or unstable particles of a given entity is reduced by half by disintegration. The half-life of $^{14}C$ is 5730 years.

In view of this half-life (T1/2) of $^{14}C$, the $^{14}C$ content is regarded as constant from the extraction of the plant starting materials up to the manufacture of the amino acid or amino ester and even up to the end of its use.

An amino acid or amino ester results in part from renewable starting materials if it comprises at least 20% by weight of C of renewable origin, preferably at least 50% by weight of C of renewable origin. The applicant regards an amino acid or amino ester as resulting from renewable starting materials and thus being "bio" if it comprises between $0.6\times10^{-10}$% and $1.2\times10^{-10}$% by weight of $^{14}C$.

There currently exist at least two different techniques for measuring the $^{14}C$ content of a sample:
 by liquid scintillation spectrometry:
 by mass spectrometry: the sample is reduced to graphite or to $CO_2$ gas and analyzed in a mass spectrometer. This technique uses an accelerator and a mass spectrometer to separate the $^{14}C$ ions from the $^{12}C$ ions and thus to determine the ratio of the two isotopes.

All these methods for measuring the $^{14}C$ content of the materials are clearly described in the standards ASTM D 6866 (in particular D 6866-06) and the standards ASTM D 7026 (in particular 7026-04).

The measurement method preferably used in the case of the amino acids or amino esters of the invention is the scintillation (Liquid Scintillation Counting, LSC) described in the standard ASTM D 6866-06.

The invention is illustrated by the following examples.

EXAMPLE 1

This example illustrates the first stage of ethenolysis of palmitoleic acid. This reaction is carried out at 30° C. at atmospheric pressure in the presence of a ruthenium-based catalyst [RuCl$_2$(=CHPh)(IMesH$_2$)(PCy$_3$)] using an excess of ethylene in order to obtain 9-decenoic acid $CH_2$=CH—$(CH_2)_7$—COOH. The yields are determined by chromatographic analysis. At the end of the reaction, 6 hours, the $C_8$ α-olefin is separated by vacuum distillation.

EXAMPLE 2

This example illustrates the second stage (optional) of homometathesis of the 9-decenoic acid resulting from the first stage to give the diacid of formula COOH—$(CH_2)_7$—CH=CH—$(CH_2)_7$—COOH.

Use is made, for this second stage, of the bispyridine ruthenium complex catalyst (8) described in the publication by Chen-Xi Bai et al., Tetrahedron Letters, (2005), 7225-7228. The reaction is carried out in toluene at a temperature of 50° C. and for 12 hours under a pressure of 50 kPa, the ethylene formed being extracted during the reaction. The yield is 90 mol %.

EXAMPLE 3

This example illustrates the oxidative cleavage by reductive ozonolysis of the 9-decenoic acid resulting from example 1.

Ozone obtained by a Welsbach T-408 ozone generator is bubbled into 25 ml of pentane until a blue color is observed. The pentane solution is kept at −70° C. with an acetone/dry ice bath. 20 mg of methyl ester, dissolved in 5 ml of pentane cooled to 0° C., are added to the ozone solution. The excess ozone is subsequently removed and the blue color disappears. After 5 minutes, the pentane is evaporated with a stream of dry nitrogen. During this stage, the temperature of the solution is kept below 0° C. After evaporating the pentane, 3 ml of methanol cooled to −70° C. are added to the reactor while reheating it in order to make possible the dissolution of the ozonide. The clear solution is cooled to −70° C. and then 2 ml of DMS are added. The reactor is reheated from time to time to make possible correct dissolution of the precipitates which may be formed. The solution is maintained at −70° C. for 20 minutes and is subsequently slowly reheated. It is maintained at 0° C. for 15 minutes before being brought to ambient temperature. The excess DMS is evaporated under a stream of dry nitrogen and the methanol is subsequently evaporated under vacuum. 9-Oxononanoic acid is obtained with a yield of 50 mold with respect to the theoretical yield.

EXAMPLE 4

This example illustrates the oxidative cleavage by reductive ozonolysis of the $C_{18}$ diacid resulting from example 2.

1 mg of the diester of oleic acid, dimethyl octadec-9-ene-1,18-dioate, is dissolved in 2 ml of pentane saturated with ozone and precooled to −70° C. The pentane is evaporated under a stream of nitrogen and 1 ml of DMS is added to the ozonide obtained. After 30 minutes, the excess DMS is evaporated under a stream of nitrogen. The product is dissolved in a small amount of ether and is analyzed.

The yield of methyl 9-oxononanoate ester is 82 mol %.

EXAMPLE 5

This example illustrates stages 2 and 3 of the process (without homometathesis) and in particular the amino reduction of the aldehyde functional group of the ω-oxononanoic acid.

530 g of 9-decenoic acid, 1600 ml of methanol and 35 ml of concentrated sulfuric acid are heated at reflux for 6 hours in a 2 liter round-bottom flask surmounted by a reflux condenser. On cooling, the mixture separates into two parts: the methyl decenoate and the excess methanol. Most of the alcohol is removed with a filter pump and then the supernatant decenoate is separated by settling from the remaining alcohol. Water is added to this alcohol and extraction is carried out with ether. The ethereal solutions and the methyl decenoate are mixed and washed with water, then with a sodium bicarbonate solution and finally with water. Drying is carried out over sodium sulfate, the ether is evaporated, the remaining alcohol is driven off using a filter pump and distillation is carried out using a vane pump. 526 g of very slightly yellow decenoate are collected.

Ozonized oxygen (T23 ozonizer from Trailigaz-Welsbach) passes at a flow rate of 100l/h through a solution of 100 g of decenoate in 100 cc of glacial acetic acid. The ozonization lasts 7 hours and is monitored by the coloring of a 2% potassium iodide solution. The stream of ozone is halted when iodine precipitates and when a potassium iodide solution diverted onto the outlet circuit of the gases instantaneously turns yellow. If the ozone is halted as soon as the red color appears in the first solution, the ozonization is incomplete, as is proved by the decoloration of a solution of bromine in glacial acetic acid by a drop of the solution to be ozonized.

The ozonization is exothermic and the solution to be ozonized has to be cooled with water. When the reaction is complete, a stream of oxygen flushes the entire apparatus for half an hour and drives off, inter alia, the ozone dissolved in the acetic acid solution. This solution is diluted with 400 ml of ether and poured into a 2 liter three-necked round-bottomed flask equipped with a stirrer and a reflux condenser. Stirring is carried out and 10 g of zinc powder with 0.5 ml of water are run in at once, followed by 90 g of zinc in small portions and, finally, 10 ml of water dropwise.

The rate at which the zinc powder and the water have to be added depends on the strength of the decomposition and cooling may sometimes be necessary. After addition of the zinc and water, the mixture is refluxed until it no longer gives a blue coloring when a drop is stirred with a solution of potassium iodide and of thiodene.

The zinc acetate is then filtered off on a Büchner funnel and carefully washed with ether. The filtrate and the washing solutions are stirred twice with 500 ml of water, once with 200 ml and with a 10% sodium carbonate solution and finally with water. Drying is carried out with sodium sulfate, the ether is driven off and distillation is carried out with a filter pump and then with a vane pump.

Four fractions are thus collected: a top fraction comprising the light aldehydes, an intermediate fraction, a fraction rich in aldehyde ester and a tail fraction. The yield of aldehyde ester is 75 mol %.

50 g of aldehyde ester, 50 ml of liquid ammonia, 125 ml of alcohol and 6 g of Raney nickel are run into a 500 ml stainless steel autoclave.

The hydrogen is introduced at a pressure of 100 to 150 atmospheres and the autoclave is heated at 100-110° C. for 4 hours. On cooling, the hydrogen and the ammonia are driven off, the contents are siphoned out and the autoclave is rinsed with the alcohol. The contents of the autoclave and the washing alcohol are combined, filtered through a Büchner funnel and placed in a vacuum distillation apparatus in the presence of nitrogen. The alcohol and the ammonia are driven off with a filter pump and then with a vane pump. The crude colored amino ester is placed in a dropping funnel for the purpose of the distillation thereof in the apparatus described.

The distilled amino ester (38 g) is slightly colored. The yield is 76% mol %.

The amino ester can optionally be directly polymerized to give polyimide-9, by heating under vacuum in order to recover the methanol produced.

The amino acid can also be polymerized. For this, the amino ester is hydrolyzed. The methyl 9-aminononanoate obtained from 28 g of aldehyde ester is placed in a dropping funnel in order to fall dropwise into a 2 liter three-necked round-bottomed flask which is surmounted by a long distillation column and which contains one liter of boiling water. Reflux is adjusted so as to distill off the methanol formed, which makes it possible to monitor the reaction; the hydrolysis lasts from 4 to 5 hours for the methyl ester. When the reaction is complete, filtration is carried out under hot conditions and the water is evaporated. A product is obtained which is difficult to dry in a desiccator whereas, on washing the wet product with acetone and drying it in a desiccator, 20 g of crude colorless amino acid are collected.

What is claimed is:

1. A process for the synthesis of amino acids or amino esters of the general formula $NH_2$—$(CH_2)_8$—COOR, R being either H or an alkyl radical comprising from 1 to 4 carbon atoms, from long-chain natural unsaturated fatty acids or esters corresponding to the formula $R_1CH$=$CH$—$(CH_2)_7$—COOR in which $R_1$ represents either H or a hydrocarbon radical comprising from 1 to 11 carbon atoms having from 0 to 2 olefinic unsaturations and, optionally one hydroxyl functional group, comprising (a) subjecting said unsaturated fatty acid or ester to a catalytic cross metathesis reaction with ethylene to form ω-unsaturated acids or esters, at least 50 mol% of which correspond to formula $CH_2=CH-(CH_2)_7-COOR$, thereafter;

(b) subjecting the acid or ester of the formula $CH_2=CH-(CH_2)_7-COOR$ to an oxidative cleavage reaction to form an aldehyde acid/ester of formula $CHO-(CH_2)_7-COOR$ and thereafter;

(c) converting the resulting aldehyde acid/ester of formula $CHO-(CH_2)_7-COOR$ by reductive amination to give an ω-amino acid/ester of formula $NH_2-(CH_2)_8-COOR$.

2. The process as claimed in claim 1, characterized in that the oxidative cleavage is carried out by reductive ozonolysis.

3. The process as claimed in claim 2, characterized in that the reductive ozonolysis is in the presence of a zinc metal.

4. The process as claimed in claim 2, characterized in that the reductive ozonolysis is in the presence of a dimethyl sulfide.

5. A process for the synthesis of amino acids or amino esters of the general formula $NH_2-(CH_2)_8-COOR$, R being either H or an alkyl radical comprising from 1 to 4 carbon atoms, from long-chain natural unsaturated fatty acids or esters corresponding to the formula $R_1CH=CH-(CH_2)_7-COOR$ in which $R_1$ represents either H or a hydrocarbon radical comprising from 1 to 11 carbon atoms having from 0 to 2 olefinic unsaturations and, optionally one hydroxyl functional group, comprising (a) subjecting said unsaturated fatty acid or ester to a catalytic cross metathesis reaction with ethylene to form a medium comprising ω-unsaturated acids or esters, at least 50 mol% of which correspond to formula $CH_2=CH-(CH_2)_7-COOR$, thereafter;

(b) separating α-olefin from said medium and subjecting the unsaturated acid/ester of formula $CH_2=CH-(CH_2)_7-COOR$ to a homometathesis to form diacid (diester) of formula $ROOC-(CH_2)_7-CH=CH-(CH_2)_7-COOR$;

(c) subjecting the diacid (diester) of the formula $ROOC-(CH_2)_7-CH=CH-(CH_2)_7-COOR$ to an oxidative cleavage reaction to form an aldehyde acid of formula $CHO-(CH_2)_7-COOR$ and thereafter;

(d) converting the resulting aldehyde acid of formula $CHO-(CH_2)_7-COOR$ by reductive amination to give an ω-amino acid/ester of formula $NH_2-(CH_2)_8-COOR$.

* * * * *